United States Patent
Masui et al.

(10) Patent No.: US 8,867,813 B2
(45) Date of Patent: Oct. 21, 2014

(54) ULTRASONIC IMAGING DEVICE, ULTRASONIC IMAGING METHOD AND PROGRAM FOR ULTRASONIC IMAGING

(75) Inventors: Hironari Masui, Musashino (JP); Takashi Azuma, Sagamihara (JP)

(73) Assignee: Hitachi Medical Corporation, Tokyo (JP)

( * ) Notice: Subject to any disclaimer, the term of this patent is extended or adjusted under 35 U.S.C. 154(b) by 182 days.

(21) Appl. No.: 13/503,858

(22) PCT Filed: Oct. 26, 2010

(86) PCT No.: PCT/JP2010/068988
§ 371 (c)(1),
(2), (4) Date: Apr. 25, 2012

(87) PCT Pub. No.: WO2011/052602
PCT Pub. Date: May 5, 2011

(65) Prior Publication Data
US 2012/0224759 A1  Sep. 6, 2012

(30) Foreign Application Priority Data
Oct. 27, 2009 (JP) ................................ 2009-246734

(51) Int. Cl.
G06K 9/00 (2006.01)
G06K 9/32 (2006.01)
A61B 8/08 (2006.01)
G06T 7/00 (2006.01)

(52) U.S. Cl.
CPC ....... *A61B 8/085* (2013.01); *G06T 2207/30096* (2013.01); *G06K 9/3233* (2013.01); *G06T 7/0014* (2013.01); *A61B 8/5269* (2013.01); *G06T 2207/10132* (2013.01)
USPC ........................................................ 382/131

(58) Field of Classification Search
None
See application file for complete search history.

(56) References Cited

U.S. PATENT DOCUMENTS

2006/0052702 A1   3/2006   Matsumura et al.
2008/0077011 A1   3/2008   Azuma et al.

FOREIGN PATENT DOCUMENTS

| JP | 2002-222410 | 8/2002 |
| JP | 2004-57275 | 2/2004 |
| JP | 2004-121834 | 4/2004 |
| JP | 2004-129773 | 4/2004 |
| JP | 2004-135929 | 5/2004 |
| JP | 2004-351050 | 12/2004 |
| JP | 2008-79792 | 4/2008 |
| WO | WO 2010/052868 A1 | 5/2010 |

*Primary Examiner* — Atiba O Fitzpatrick
(74) *Attorney, Agent, or Firm* — Antonelli, Terry, Stout & Kraus, LLP.

(57) ABSTRACT

An ultrasonic imaging apparatus is provided, discriminates a noise area where echo signals are faint, by selecting a reference frame and a comparative frame from an image obtained by processing received signals and including a plurality of frames. A region of interest is set in the reference frame, a search area wider than the region of interest is set in the comparative frame, and multiple candidate regions being destination candidates of the region of interest are set within the search area. A degree of similarity between an image characteristic value in the region of interest and an image characteristic value in the candidate region is calculated, with respect to each of the candidate regions, to obtain a distribution of the degrees of similarity across the search area. Based on the similarity distribution, whether or not the region of interest corresponds to the noise area is determined.

10 Claims, 17 Drawing Sheets (a) B-MODE IMAGE

LOW S/N REGION (b) IMAGE OF MOTION VECTOR MAP

DEGREE OF SEPARATION IMAGE

(a) MOTION VECTOR MAP (b) EXAMPLE OF ERROR VECTOR REMOVAL (a) IMAGE OF ORIGINAL SAD DISTRIBUTION (b) LPF (Low Pass Filter) PROCESS (c) DIFFERENCE BETWEEN SAD DISTRIBUTION AND LPF PROCESS DISTRIBUTION

ULTRASONIC IMAGING DEVICE, ULTRASONIC IMAGING METHOD AND PROGRAM FOR ULTRASONIC IMAGING

TECHNICAL FIELD

The present invention is directed to a technique relating to an ultrasonic imaging method and an ultrasonic imaging apparatus which allow a tissue boundary to be clearly discerned, upon imaging a living body through the use of ultrasonic waves.

BACKGROUND ART

As described in the Patent Document 1, for instance, in an ultrasonic imaging apparatus used for medical imaging diagnosis, there is known a method which estimates a distribution of modulus of elasticity of tissue, based on a change amount within a small area in a diagnostic moving image (a B-mode image), and converts stiffness into a color map for display. However, byway of example, in the case of a peripheral zone of a tumor, neither acoustic impedance nor the modulus of elasticity may show a major difference, relative to the surrounding tissue. In this case, it is not possible to figure out a boundary between the tumor and the surrounding tissue, in the diagnostic moving image nor in the elasticity image.

The technique described in the Patent Document 2 suggests a method which generates a scalar field image directly from motion vectors of a diagnostic moving image, thereby allowing a tissue boundary to be discerned, when neither the acoustic impedance nor the modulus of elasticity are largely different relative to the surroundings.

PRIOR ART DOCUMENT

Patent Document

Patent Document 1
Japanese Unexamined Patent Application Publication No. 2004-135929
Patent Document 2
Japanese Unexamined Patent Application Publication No. 2008-79792

DISCLOSURE OF THE INVENTION

Problem to be Solved by the Invention

According to the technique described in the conventional Patent Document 2, two pieces of diagnostic image data are subjected to a block matching process, so as to estimate the motion vectors. However, when the estimation is performed, an error vector may be generated due to an effect of noise in the image data. Therefore, there has been a problem that a discrimination degree of a boundary is degraded. In particular, in a marginal domain of signal penetration where echo signals become faint, estimate precision of the vectors is drastically deteriorated.

An object of the present invention is to provide an ultrasonic imaging apparatus which is capable of discriminating a noise area where echo signals are faint.

Means to solve the Problem

In order to achieve the object above, according to a first aspect of the present invention, an ultrasonic imaging apparatus as described below is provided. In other words, the ultrasonic imaging apparatus of the present invention includes a transmitter for transmitting ultrasonic waves directed to an object, a receiver for receiving ultrasonic waves coming from the object, and a processor for processing received signals of the receiver to generate an image made up of two or more frames. The processor assumes one frame out of the two or more frames being generated, as a reference frame, and sets a region of interest (ROI) at either of a predetermined position and a position being accepted from an operator. In addition, the processor assumes one of the other frames as a comparative frame, sets a search area wider than the ROI at either of a predetermined position and a position being accepted from the operator, and further sets in the search area, multiple candidate regions which are destination candidates of the ROI. The processor calculates a degree of similarity of an image characteristic value between in the ROI and in the candidate region, with respect to each of the candidate regions, and obtains a similarity distribution across the search area. Accordingly, it is possible to determine whether or not the ROI corresponds to a noise area, based on the similarity distribution.

For example, the processor has a configuration for obtaining statistics that compares a minimum value of the degree of similarity with an overall value thereof in the similarity distribution, and determining confidence of the ROI according to thus obtained statistics. Specifically, for instance, the processor obtains the aforementioned statistics by using the minimum value, a mean value, and a standard deviation of the degree of similarity, and compares thus obtained statistics with a threshold value, thereby enabling determination of confidence of the ROI.

For example, the processor is capable of generating a vector which connects a position associated with the ROI in the comparative frame, to a position of the candidate region with the minimum degree of similarity, and substitutes zero or a predetermined vector for the vector with regard to the ROI being determined as having low confidence. According to this operation, it is possible to remove an error vector, and the like, thereby increasing the precision of the vector.

By way of example, the processor calculates the mean value, the minimum value, and the standard deviation of the degree of similarity, with regard to the similarity distribution, and employs as the statistics, a degree of separation which is obtained by dividing a difference between the mean value and the minimum value, by the standard deviation. In addition, it is also possible for the processor to calculate the mean value and the standard deviation of the degree of similarity, with regard to the similarity distribution, and employ as the statistics, a coefficient of variation obtained by dividing the standard deviation by the mean value.

The aforementioned threshold value used for the comparison with the statistics is obtained by the following procedure. For example, multiple regions of interest are set, and the statistics with respect to each ROI is obtained. Then, a histogram distribution representing a frequency of values of the statistics is further obtained. A median value or a mean value of the histogram distribution, or if the histogram distribution shows multiple peaks, a minimum value of the statistics associated with a trough between the peaks, is used as the threshold value.

In addition, it is possible to generate a similarity distribution after smoothing, after performing a smoothing process on the similarity distribution, and obtain a differential similarity distribution which is a result of subtraction of the similarity distribution after smoothing, from the similarity distribution prior to the smoothing process. Accordingly, it is possible to remove fluctuations in the degree of similarity caused by noise, from the similarity distribution.

As the aforementioned smoothing process, for instance, a method is employed which sets a filter of a predetermined size on the similarity distribution, and repeats the process for smoothing the distribution within the filter, while moving the filter by a predetermined distance. The size of the filter may be determined as the following. A vector is generated in advance with respect to each of multiple regions of interest, the vector connecting the position associated with the ROI in the comparative frame, to the position of the candidate region with the minimum degree of similarity in the similarity distribution prior to the smoothing. A maximum length of the vector, out of the vectors being generated, is assumed as the size of the filter.

In addition, the aforementioned similarity distribution is subjected to a filtering process using a Laplacian filter, to create a distribution of edge enhancement, and a continuous edge is extracted from the distribution of edge enhancement, whereby a boundary of the object may be obtained.

With the configuration of the processor as described in the following, it is also possible to determine a degree of invasiveness of a tumor. In other words, the processor includes a first processing means for obtaining a similarity distribution as to the ROI set near a boundary of a tumor in a living body, generating a similarity distribution image assuming the degree of similarity as an image characteristic value, and setting an one-dimensional area with a predetermined length in each of multiple different directions with a central focus on a position associated with the ROI on the similarity distribution image, a second processing means for calculating a total sum of the degrees of similarity within the one-dimensional area, with respect to each of the directions being set, a third processing means for calculating a ratio of a total sum of the degrees of similarity in the direction in which the total sum of the degrees of similarity becomes the minimum, to a total sum of the degrees of similarity of the one-dimensional area in the direction orthogonal to the direction in which the total sum of the degrees of similarity becomes the minimum, and a fourth processing means for determining the degree of invasiveness of the tumor based on the ratio.

In addition, when the ratio calculated in the third processing means is smaller than a predetermined certain value, it is determined that the pixel being focused is a point constituting the boundary, and therefore the boundary can be obtained.

According to a second aspect of the present invention, an ultrasonic imaging method is provided as described in the following. In other words, the method includes the steps of transmitting ultrasonic waves directed to an object, processing received signals obtained by receiving ultrasonic waves coming from the object, so as to generate an image made up of two or more frames, selecting a reference frame and a comparative frame from the image, setting an ROI in the reference frame, setting in the comparative frame a search area wider than the ROI, setting in the search area multiple candidate regions which are destination candidates of the ROI, and calculating a degree of similarity of an image characteristic value between in the ROI and in the candidate region, with respect to each of the multiple candidate regions, so as to obtain a similarity distribution across the search area.

According to a third aspect of the present invention, a program for ultrasonic imaging is provided as described in the following. In other words, the program for ultrasonic imaging allows a computer to execute, a first step for selecting a reference frame and a comparative frame from an ultrasonic image made up of two or more frames, a second step for setting an ROI in the reference frame and setting in the comparative frame, a search area wider than the ROI, a third step for setting within the search area, multiple candidate regions being destination candidates of the ROI, and a fourth step for calculating a degree of similarity of the image characteristic value between in the ROI and in the candidate region, with respect to each of the candidate regions, so as to obtain a similarity distribution across the search area.

Effect of the Invention

According to the present invention, it is possible to determine whether or not the ROI corresponds to a noisy area, based on the similarity distribution. This may reduce the occurrence of an error vector, thereby enabling highly accurate vector estimation even in a marginal domain of penetration. Precision of a scalar field image, obtained by converting a field of the estimated motion vectors, is enhanced, thereby allowing the boundary to be detected more appropriately.

PREFERRED EMBODIMENTS OF THE INVENTION

Hereinafter, the ultrasonic imaging apparatus according to one embodiment of the present invention will be explained.
(First Embodiment)

Figure 1:
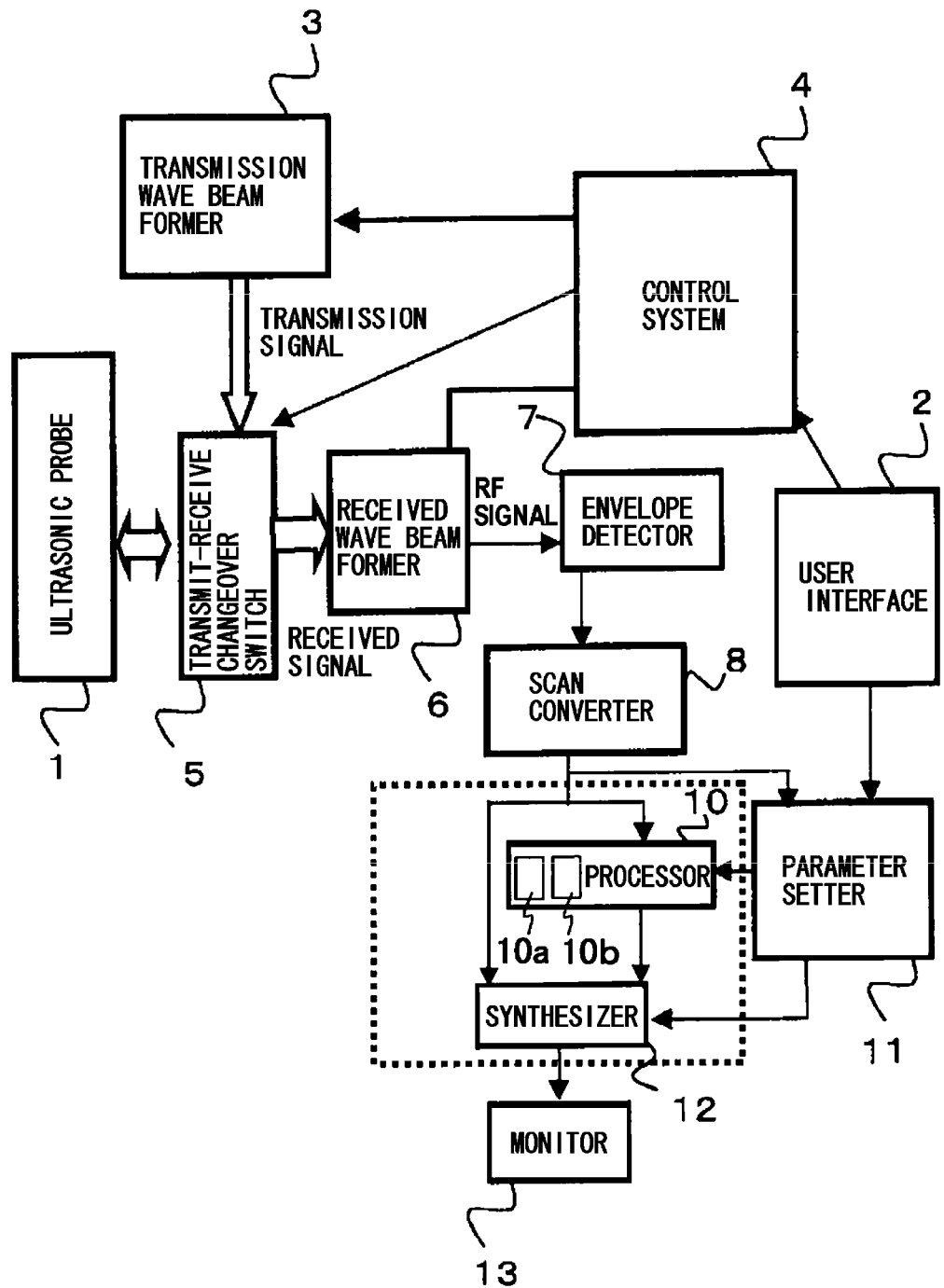
FIG. 1 is a block diagram showing a system configuration example of the ultrasonic imaging apparatus according to the first embodiment.

FIG. 1 illustrates a system configuration of the ultrasonic imaging apparatus according to the present embodiment. The present apparatus is provided with a function of ultrasonic boundary detection. As shown in FIG. 1, the present apparatus incorporates an ultrasound probe (probe) 1, user interface 2, a transmission wave beam former 3, a control system 4, a transmit-receive changeover switch 5, a received wave beam former 6, an envelope detector 7, a scan converter 8, a processor 10, a parameter setter 11, a synthesizer 12, and a monitor 13.

The ultrasound probe 1 in which ultrasonic elements are arranged one dimensionally, transmits an ultrasonic beam (an ultrasonic pulse) to a living body, and receives an echo signal (a received wave signal) reflected from the living body. Under the control of the control system 4, the transmission wave beam former 3 outputs a transmission signal having a delay time being adjusted to a transmit focus, and the signal is transferred to the ultrasound probe 1 via the transmit-receive changeover switch 5. The ultrasonic beam being reflected or scattered within the living body and returning to the ultrasound probe 1 is converted into an electrical signal by the ultrasound probe 1, and transmitted to the received wave beam former 6 as a received wave signal, via the transmit-receive changeover switch 5.

The received wave beam former 6 is a complex beam former for mixing two received wave signals which are out of phase by 90 degrees, performing a dynamic focusing to adjust the delay time in accordance with a receive timing under the control of the control system 4, so as to output radio frequency signals corresponding to the real part and the imaginary part. The envelope detector 7 detects the radio frequency signals, then converts the signals into video signals, inputs the video signals into the scan converter 8, so as to be converted into image data (B-mode image data). The configuration described above is the same as the configuration of a well known ultrasonic imaging apparatus.

In the apparatus according to the present invention, the processor 10 implements the ultrasonic boundary detection process. The processor 10 includes a CPU 10a and a memory 10b, and the CPU 10a executes programs stored in advance in the memory 10b, so as to detect a tissue boundary of a test object according to the processing below. In other words, the processor 10 initially generates a motion vector field, based on the image data made up of at least two frames, the image data being outputted from the converter 8. Next, the processor performs a process for converting the motion vector field being generated into a scholar field. Then, the synthesizer 12 synthesizes original image data and the motion vector field or the scalar field, being associated with the original image data, and thereafter the monitor 13 makes a display thereof.

The parameter setter 11 performs processing such as selecting and setting, parameters used for signal processing in the processor 10 and an image for display being provided by the synthesizer 12. An operator (device manipulator) inputs those parameters from the user interface 2. For example, as the parameters for the signal processing, it is possible to accept from the operator, a setting of an ROI on a desired frame m, and a setting of a search area on the frame m+Δ, which is different from the frame m. As the selecting and setting of the image for display, for instance, it is possible to accept from the operator, a selecting and setting whether the original image and the vector field image (or the scalar image) are synthesized into one image to be displayed on the monitor, or two or more moving picture images are displayed side by side.

Figure 2:
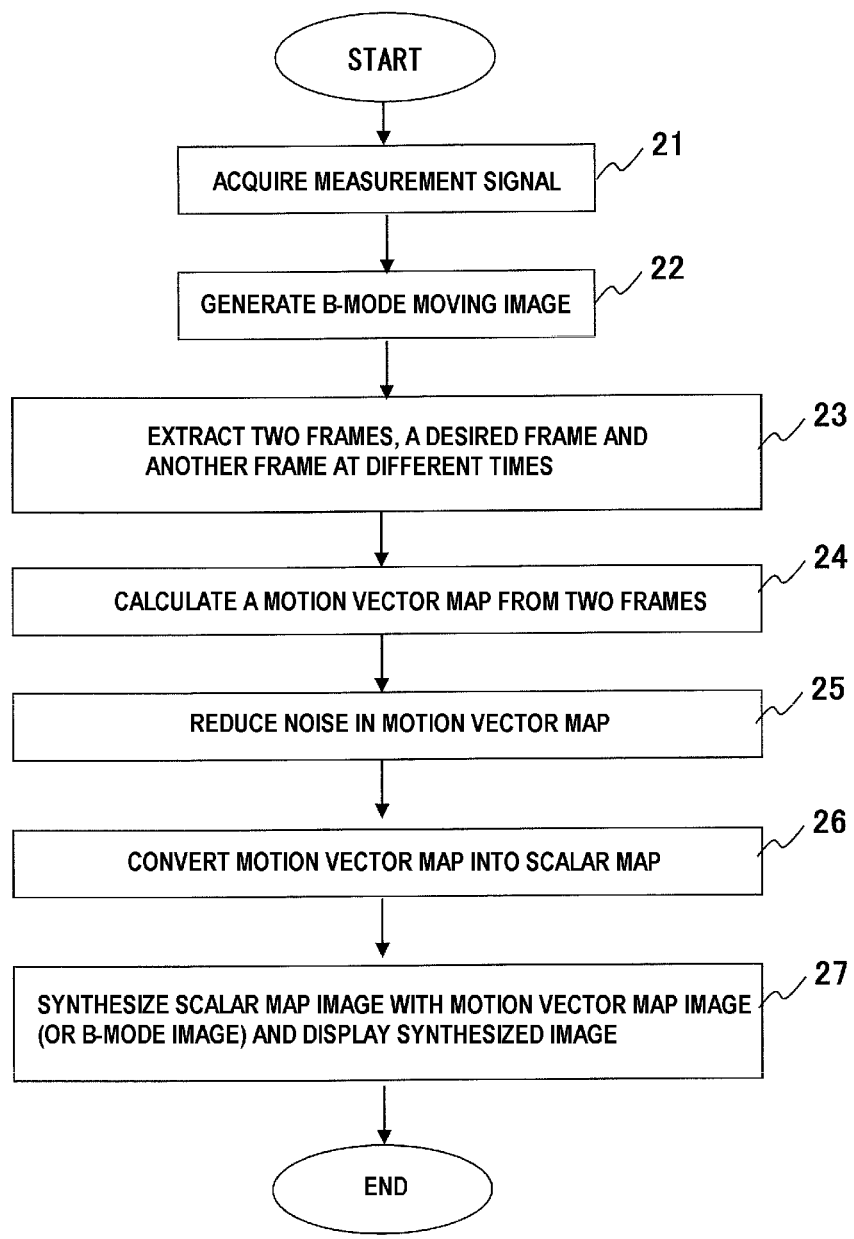
FIG. 2 is a flowchart showing a processing procedure of image generation by the ultrasonic imaging apparatus according to the first embodiment.

FIG. 2 is a flowchart showing one example of the boundary detecting process and the image processing in the processor 10 and the synthesizer 12 according to the present invention. The processor 10 firstly acquires a measured signal from the scan converter 8, and subjects the signal to a normal signal processing to generate a B-mode moving image (steps 21 and 22). Next, the processor extracts two frames from the B-mode moving image, a desired frame and another frame at a time different therefrom (step 23). For example, there are extracted two frames, a desired frame and a frame subsequent thereto. Then, the processor calculates a motion vector field from those two frames (step 24). The calculation of the motion vector field is carried out based on a block matching method. The motion vector field being calculated is subjected to a noise reduction process (step 25), and the motion vector field in which the noise has been reduced is converted into a scalar field (step 26). Then, the processor synthesizes the scalar field image with the motion vector field image or the B-mode image, displays the synthesized image, and terminates the process for one image (step 27). The processes from the step 21 to the step 27 are repeated, while various frames are selected as the desired frame sequentially in time series in the step 23, and synthesized images are successively displayed, thereby allowing a moving image of the synthesized images to be displayed.

Figure 3:
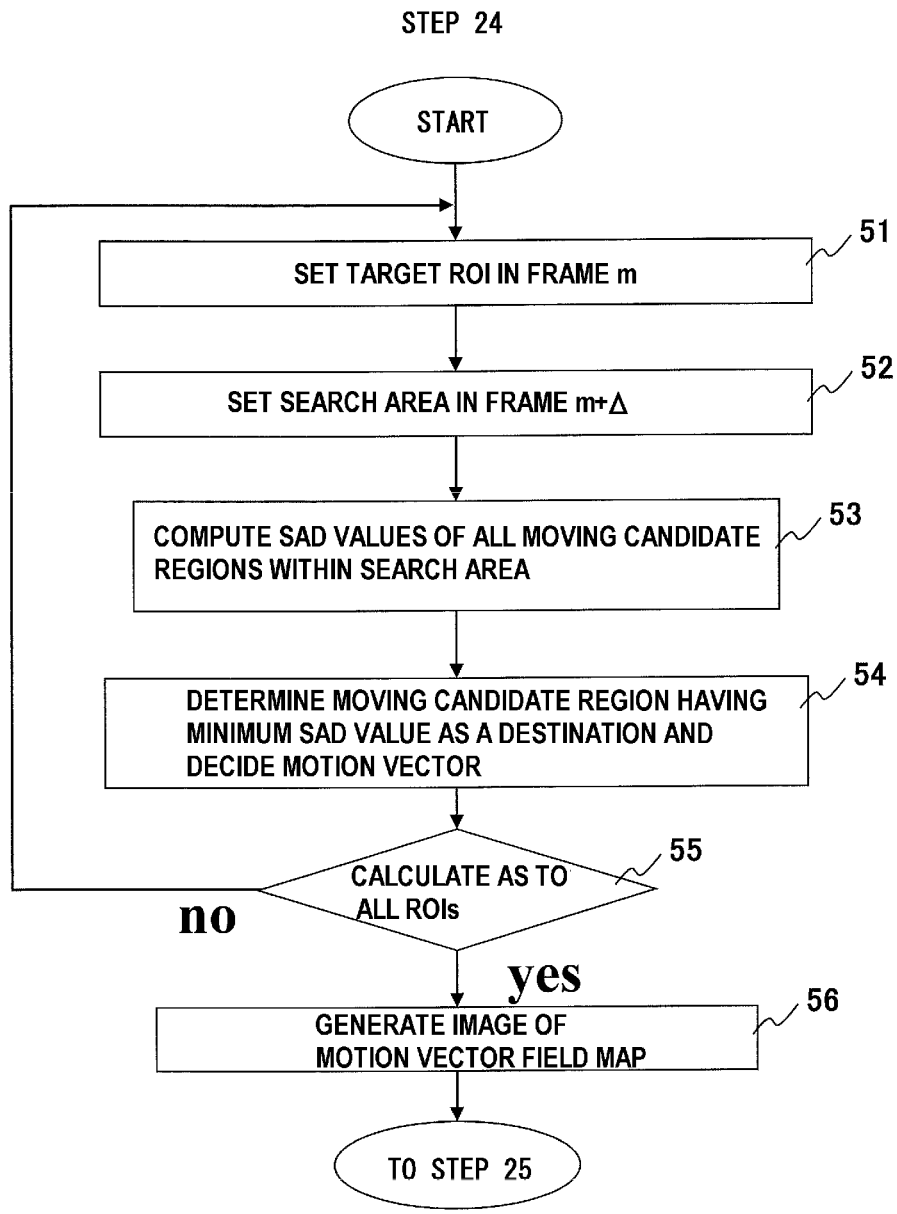
FIG. 3 is a flowchart showing the details of a block matching process of the step 24 in FIG. 2.
Figure 4:
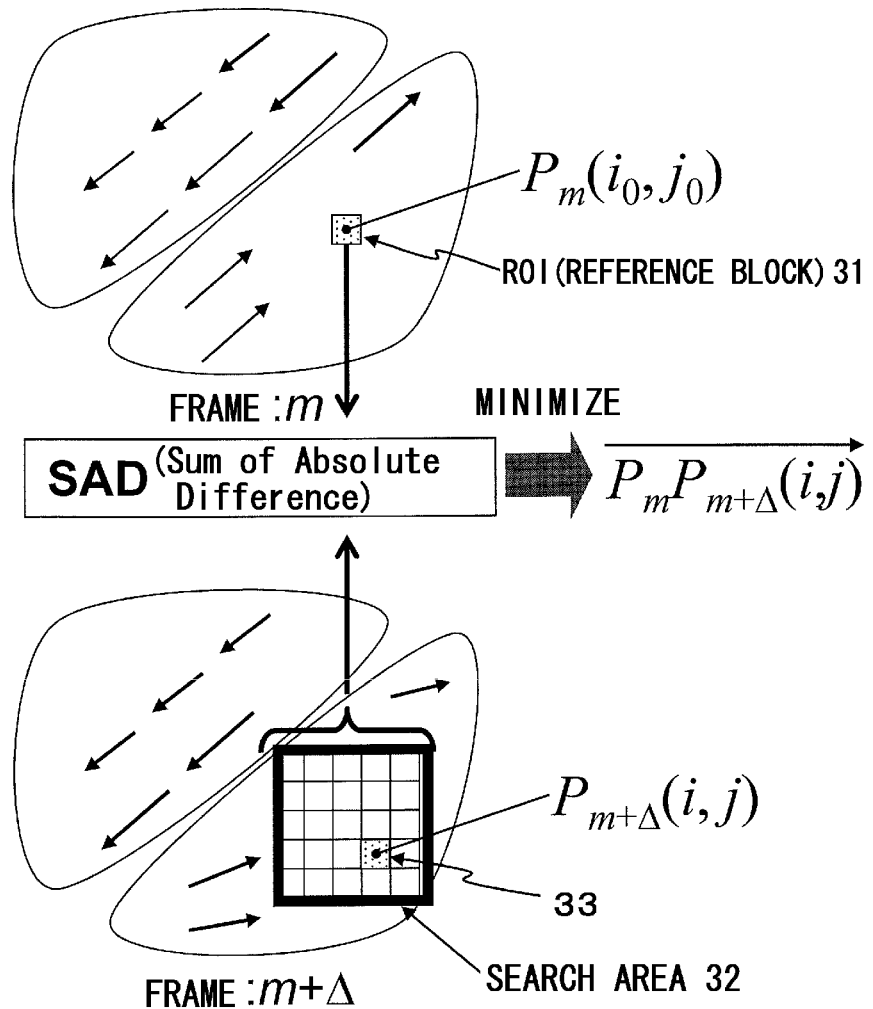
FIG. 4 illustrates the block matching process of the step 24 in FIG. 2, through the use of a two-layered phantom.

FIG. 3 is a flowchart showing a detailed process of the step 24, and FIG. 4 illustrates the block matching process of the step 24. With reference to FIG. 3 and FIG. 4, a specific explanation will be made, as to the block matching process for calculating the motion vector field in the aforementioned step 24. Here, it is assumed that the $m^{th}$ frame and the $(m+\Delta)^{th}$ frame are selected in the step 23. For example, it is assumed Δ=1 frame. Initially, the processor 10 sets in the $m^{th}$ frame, the ROI (region of interest: a reference block) 31 corresponding to a predetermined pixel count N, as shown in FIG. 4 (step 51). A brightness distribution of the pixels included in the ROI 31 are represented by $P_m(i_0, j_0)$. Here, $i_0$ and $j_0$ represent a position of the pixel within the ROI 31. Next, the processor 10 sets in the $(m+\Delta)^{th}$ frame, a search area 32 with a predetermined size, at the position associated with the ROI 31 of the $m^{th}$ frame and in proximity thereto (step 52). Here, as for the setting of the ROI 31, there will be explained a configuration that the processor 10 sets the ROI 31 sequentially across the image of the $m^{th}$ frame, and sets the search area 32 having a predetermined size assuming the ROI 31 as a center. However, it is alternatively possible that the processor 10 sets the ROI 31 of a predetermined size at a predetermined position, and the search area 32 having a predetermined size in proximity to the ROI 31, or the processor 10 sets the ROI 31 and the search area 32 respectively at the region of interest (ROI) and the search area which the parameter setter 11 accepted from the operator.

The search area 32 is partitioned into multiple moving candidate regions 33 each having the same size as the ROI 31. The processor 10 obtains by calculation a moving candidate region 33 having the highest degree of similarity relative to the brightness of the ROI 31, and selects the obtained candidate as a destination area. As an index indicating the degree of similarity, SAD (Sum of Absolute Difference), a mean squared value, a cross-correlation value, or the like, may be employed. By way of example here, an explanation will be made as to the case where the SAD is employed.

The brightness distribution of the pixels included in the moving candidate region 33 within the search area 32 is represented by $P_{m+\Delta}(i, j)$. Here, (i, j) indicates the position of the pixel within the moving candidate region 33. The processor 10 calculates a sum of absolute difference SAD between the brightness distribution $P_m(i_0, j_0)$ of the pixels within the ROI 31, and the brightness distribution $P_{m+\Delta}((i, j)$ in the moving candidate region 33 (step 53). Here, the SAD is defined according to the following formula (1):

[Formula 1]

$$SAD = \sum_{i,j} |p_m(i_0, j_0) - p_{m+\Delta}(i, j)| \quad (1)$$

The processor 10 obtains a value of SAD between the ROI 31 and each of all the moving candidate regions 33 within the search area 32, determines as the destination area, the moving candidate region 33 with the minimum SAD value in the SAD distribution being obtained, and decides a motion vector which connects the position of ROI 31 with the position of the moving candidate region 33 of the minimum SAD value (step 54).

Then, the processor 10 repeats the process above while moving the ROI 31 across the image of the frame m, thereby deciding the motion vectors for the overall image of the frame m (step 55). By creating an image which represents the vectors thus decided, for instance, by using arrows, a motion vector field (a motion vector map image) is obtained.

Figure 5:
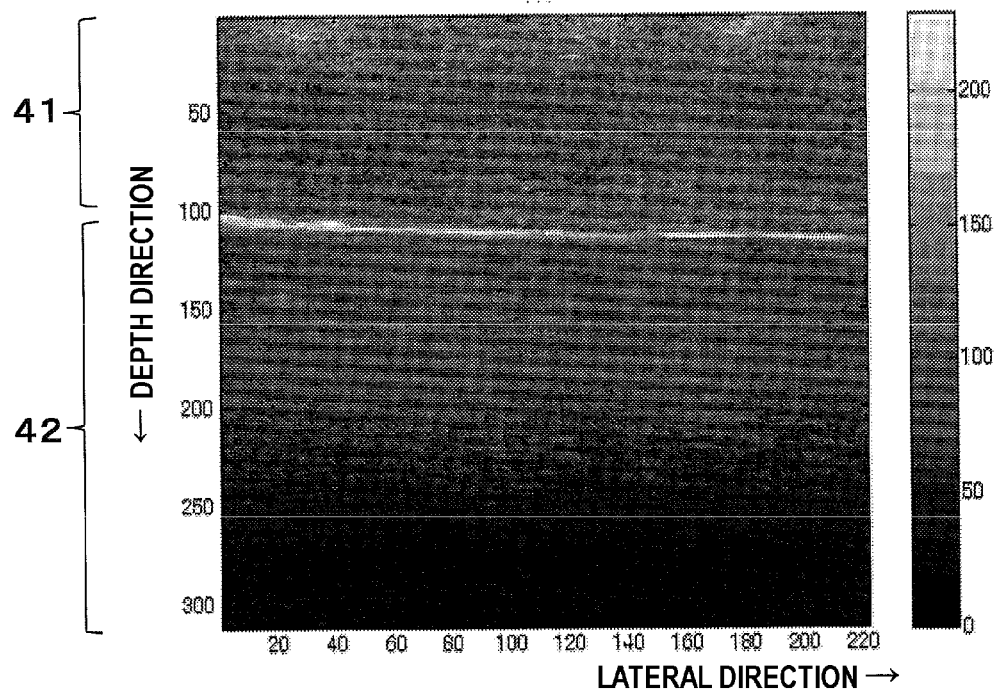
FIG. 5(a) illustrates an example of B-mode image generated by the ultrasonic imaging apparatus according to the first embodiment.
FIG. 5(b) illustrates an example of image of motion vector map generated by the ultrasonic imaging apparatus according to the first embodiment.
Figure 5:
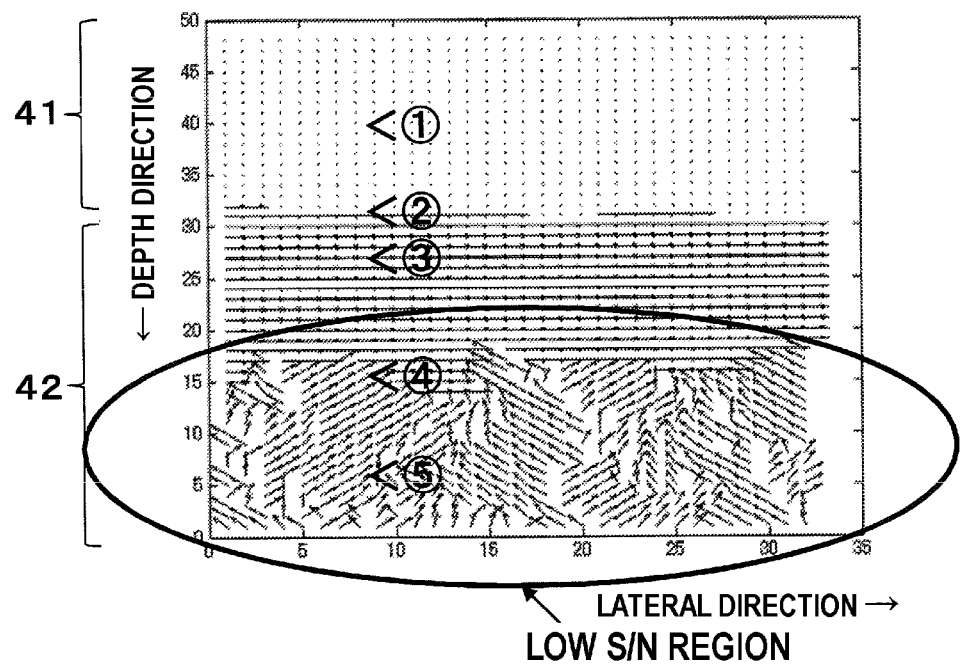

FIGS. 5(a) and (b) illustrate an example of the B-mode image and an example of the motion vector map image, obtained in the process above. Phantoms 41 and 42 of gel base material are superimposed one on another in two layers, and the B-mode image of FIG. 5(a) is taken, while moving in a lateral direction the ultrasonic probe set on the upper phantom 41. The B-mode image of FIG. 5(a) is assumed as the frame m, and FIG. 5(b) illustrates the motion vectors obtained by the block matching process (step 24) with a subsequent frame (frame m+Δ, Δ=1 frame).

As shown in FIG. 5(b), an upper area of around one-third, which corresponds to the upper phantom 41 to which the ultrasonic probe 1 is set shows the static state, relatively, and the lower phantom 42 represents a vector field (laterally directed arrows) indicating lateral movement. However, an area corresponding to lower one-third, corresponding to a part of the lower phantom 42, shows that the arrows indicate an obliquely upward direction, variably oriented, and present a phenomenon that the motion vectors fall into disorder. This phenomenon is caused by the following; with increasing distance from the probe 1, the SN ratio (SNR) of detection sensitivity falls to a low level. This indicates a limit of penetration. In other words, error vectors are generated in the area being distant from the probe 1, where the SNR is low.

Figure 6:
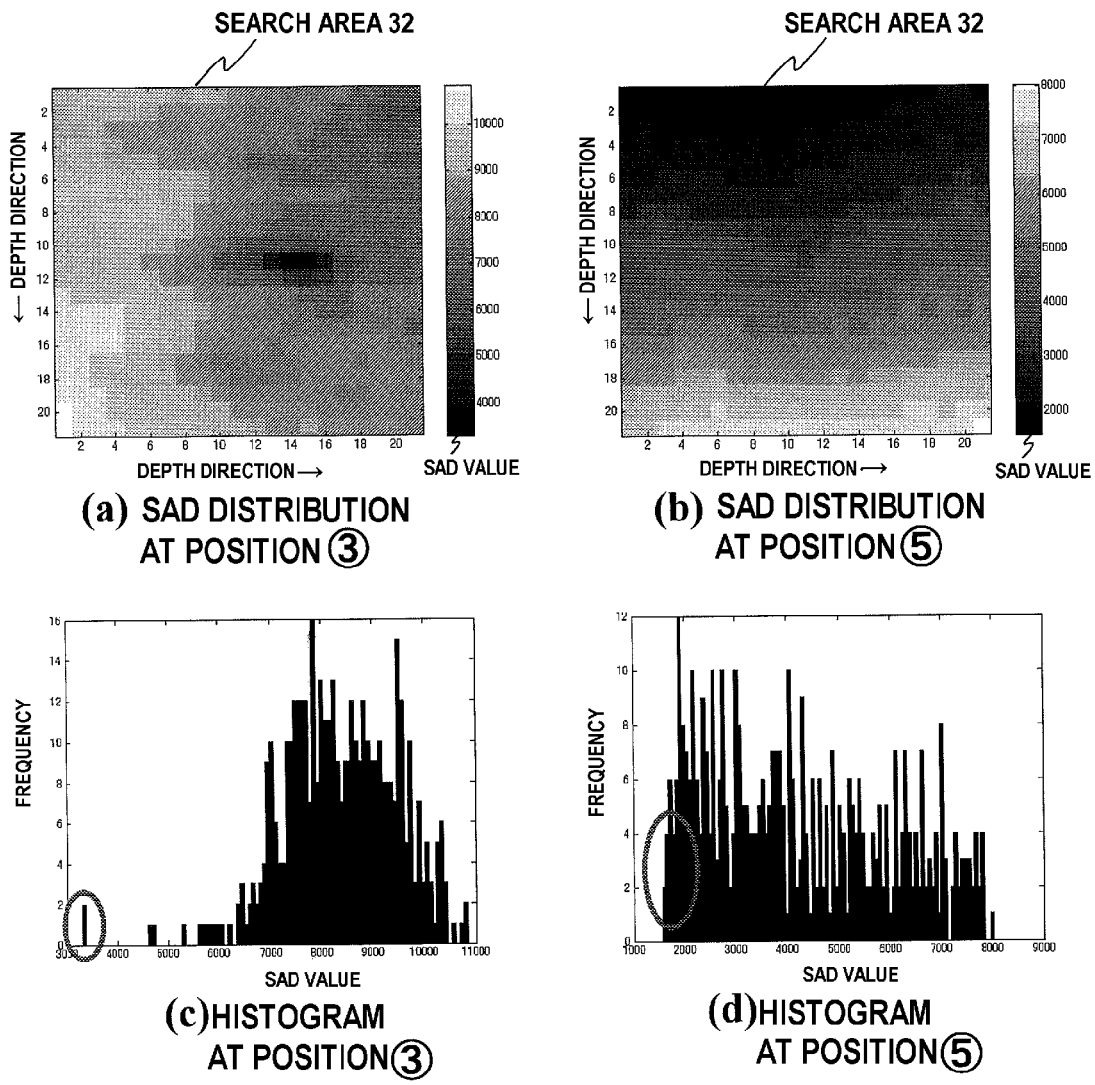
FIG. 6(a) illustrates an example of SAD (Sum of Absolute Difference) distribution image obtained by setting the ROI at the position (3) of FIG. 5(b)
FIG. 6(b) illustrates an example of SAD distribution image obtained by setting the ROI at the position (5) of FIG. 5(b)
FIG. 6(c) illustrates a histogram of the SAD values shown in FIG. 6(a)
FIG. 6(d) illustrates a histogram of the SAD values shown in FIG. 6(b)

With reference to FIG. 6, an explanation will be made as to the process for reducing noise in the motion vector field, which is performed in the aforementioned step 25.

FIGS. 6(a) and (b) are illustrations (SAD distribution charts), showing the SAD value of each moving candidate region 33 in the search area 32 obtained in the step 24, by setting the ROI 31 at each of the positions (3) and (5) in FIG. 5(b), assuming the SAD value as density of each moving candidate region 33. Each of FIGS. 6(a) and (b) represents the entire search area 32, and the search area 32 is partitioned into 21×21 moving candidate regions 33. Here, it is assumed that the block size of the moving candidate region 33 is 30×30 pixels, the size of the search area 32 is 50×50 pixels, and the moving candidate region 33 is made to move pixel by pixel within the search area 32. The search area 32 is set in such a manner that the position of the moving candidate region 33 associated with the position of the ROI 31 is positioned at the center of the search area 32.

In the SAD distribution of FIG. 6(a), the SAD value of the moving candidate region 33 located at the position displaced in the lateral direction immediately to the right side from the center of the search area 32, is the minimum. Therefore, as for the position (3) in FIG. 5(b), it is found that the vector determined in the step 24 is a vector in the right-lateral direction. As seen from FIG. 5(b), the position (3) exists in the vicinity of the place a little bit lower than the boundary between the two-layered phantoms 41 and 42 (on the side of the phantom 42), and vectors of right-lateral direction are shown.

Here, when attention is paid to the space distribution of the SAD values of FIG. 6(a), it is found that an area where the SAD value are small (a trough region of SAD values) is formed around the moving candidate region 33 with the minimum SAD value, in the lateral direction, i.e., in the direction along the boundary between the two-layered phantoms 41 and 42. This phenomenon indicates that the boundary can be directly detected from the SAD distribution of FIG. 6(a), without moving the ROI 31 across the area within the frame m to generate all the motion vector fields, as shown in FIG. 6(b).

On the other hand, the SAD distribution of FIG. 6(b) is obtained at the position (5) within the area where the motion vectors fall into disorder as shown in FIG. 5(b). Therefore, it is found that the moving candidate regions 33 where the SAD value becomes minimum spread uniformly over the upper wide area being close to the probe 1, where the noise value tends to become smaller, and the motion vectors are prone to be oriented upward with falling into disorder. It is also found that the area where the SAD values are small (the trough of SAD values), which is supposed to be formed around the moving candidate region 33 with the minimum SAD value, is indiscernible because this area is liable to be buried in overall noise fluctuations.

In the present invention, as shown in FIG. 6(a), in the SAD distribution image in which the ROI 31 is set at the position (3) where the noise is small, the moving candidate region 33 with the minimum SAD value includes the SAD values obviously smaller than the surrounding area, and therefore, it is possible to clearly discern the candidate region. On the other hand, as shown in FIG. 6(b), in the SAD distribution image of the search area 32 where the ROI 31 is set at the position (5) with much noise, the moving candidate region 33 with the minimum SAD value is not clearly discernible, and utilizing this phenomenon, the ROI 31 with much noise is discriminated. As for the ROI 31 with much noise, it is subjected to the process for removing the motion vectors being associated.

For the aforementioned discrimination, for example in the step 25 of FIG. 2, the processor 10 generates histograms indicating the distribution of the SAD values as shown in FIG. 6(c) and FIG. 6(d), respectively from the SAD distributions in the search area 32 as shown in FIG. 6(a) and FIG. 6(b) for the cases where the ROI 31 is set at predetermined positions. In the histogram for the case where the ROI 31 is set at the position (3) of FIG. 5(b), the SAD minimum value is sufficiently separated from the SAD values with high frequency in the histogram distribution shown in FIG. 6(c). In other words, the minimum SAD value is sufficiently distant from a range of the SAD values with high frequency. On the other hand, as for the histogram when the ROI 31 is set at the position (5) of FIG. 5(b), there is little difference of frequency with regard to the SAD distribution as shown in FIG. 6(d), and the histogram distribution spreads broadly. Consequently, the SAD minimum value is included in the range of the SAD values with high frequency, and thus, the minimum SAD value is not sufficiently distant from a range of the SAD values with high frequency.

With the characteristics as described above, by comparing the SAD minimum value in the histogram of the SAD distribution in the search area 32, with the SAD values with high frequency, it is possible to discriminate confidence of the ROI 31 signal (noise level low) associated with the search area 32, and confidence of the motion vectors determined in the search area 32. Consequently, an area with low confidence may be discriminated as a low SNR area, and further the confidence of associated motion vectors may be determined.

Figure 7:
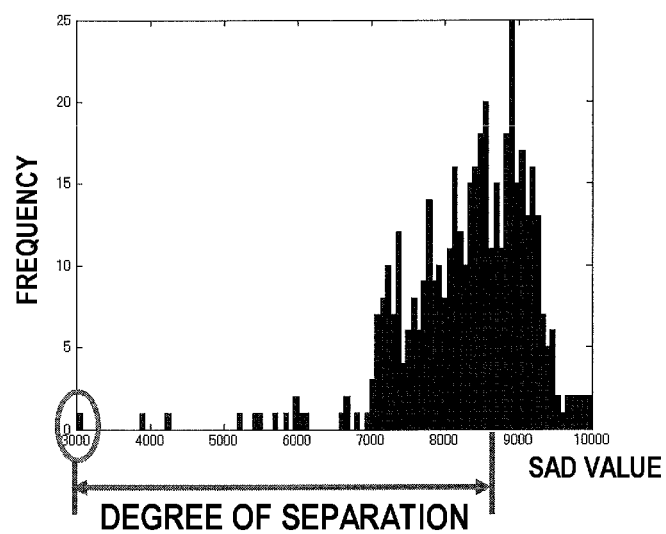
FIG. 7 illustrates on the histogram of the SAD values, a definition of a degree of separation according to the first embodiment.

According to the present invention, an index is employed to determine a degree of separation between the SAD minimum value and the SAD values with high frequency, in the histogram of the SAD distribution. Firstly, a processing method will be explained in the case where a separation degree parameter is used as the index. FIG. 7 shows a concept of the definition of the degree of separation. The degree of separation is a value corresponding to a distance between a distribution average of the histogram and the minimum value, and the value is defined by the following formula (2).

[Formula 2]

$$\text{Degree of Separation} \equiv \frac{\bar{s} - s_{min}}{\sigma_s} \quad (2)$$

$\bar{s}$: Mean SAD value
$s_{min}$: Minimum SAD value
$\sigma_s$: Standard Deviation of SAD value The formula (2) is standardized by the standard deviation, in order to avoid being influenced by variance in distribution.

Figure 8:
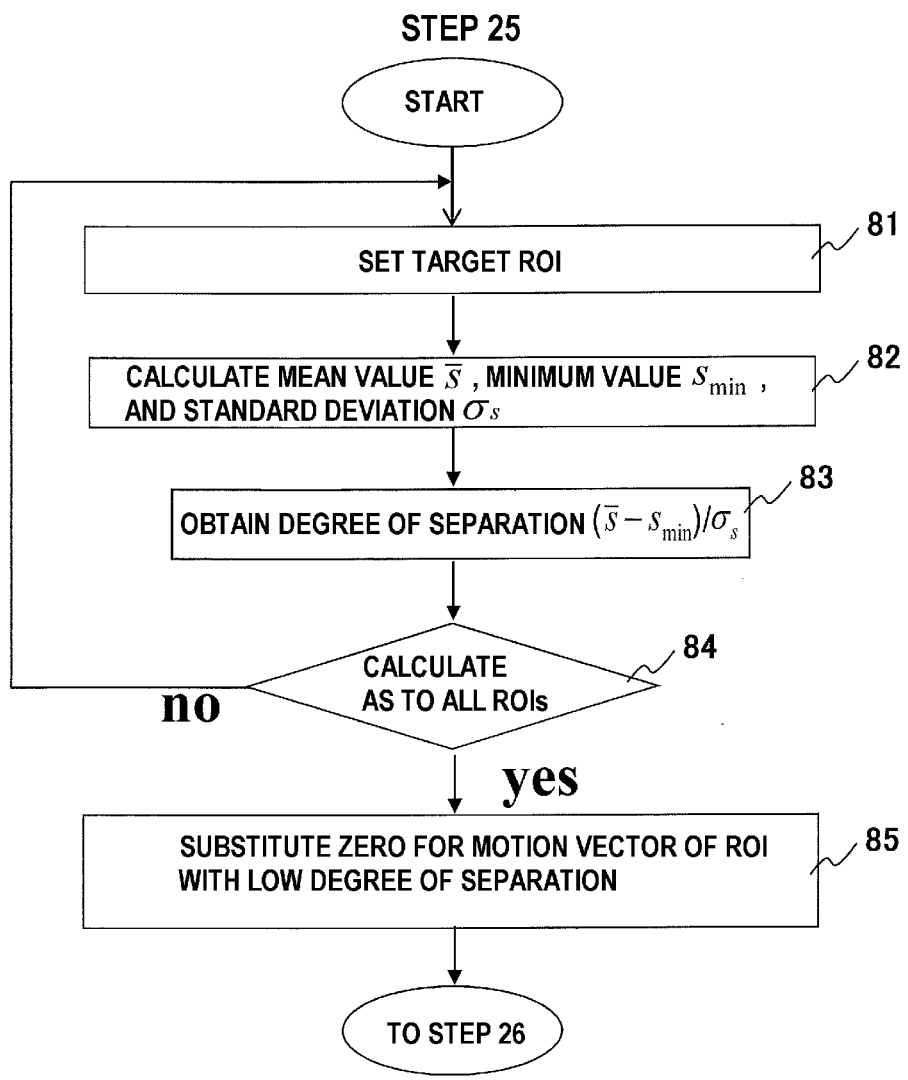
FIG. 8 is a flowchart showing the details of the process of the step 25 in FIG. 2, in the case where the process is performed through the use of the degree of separation.

FIG. 8 shows a flow of process for discriminating an area including much noise and removing motion vectors, in the case where the degree of separation is used as the index. This specifically describes the process of the step 25 in FIG. 2, and this process is performed on all of the ROIs set within the frame m in the step 51 of FIG. 3. The processor 10 determines the ROI 31 as an initial target (step 81), and calculates with respect to the ROI 31 thus determined, a mean value, a minimum vale, and a standard value of SAD values, according to a statistical process, by using the SAD values of all the moving candidate regions 33 in the search area 32 being set and computed in the steps 52 and 53 of FIG. 3 (step 82). Then, the degree of separation defined by the aforementioned formula (2) is obtained (step 83). This procedure is repeated for all the ROIs 31 (step 84). The ROI 31 with the degree of separation obtained in the step 84, being lower than a predetermined value, may be an area including much noise and motion vectors with low confidence. Therefore, the motion vectors obtained in the step 54 of FIG. 3 are replaced by zero (step 85). Accordingly, it is possible to discriminate an area with low confidence from the motion vector image, and remove vectors (error vectors).

As the predetermined value used for determining whether or not the degree of separation is low in the step 85, a predetermined threshold value or a mean value of the distribution of degrees of separation may be utilized, the degrees of separation being obtained as to all the ROIs 31 in the step 84. Alternatively, a histogram of the degrees of separation being obtained is generated, and if there are formed multiple peaks of frequency, it is possible to use as a threshold value, the degree of separation at the position of a trough, between the peak of frequency located on the side with the degrees of separation including the lowest one, and the peak of frequency located on the side where the degrees of separation are relatively higher.

Figure 9:
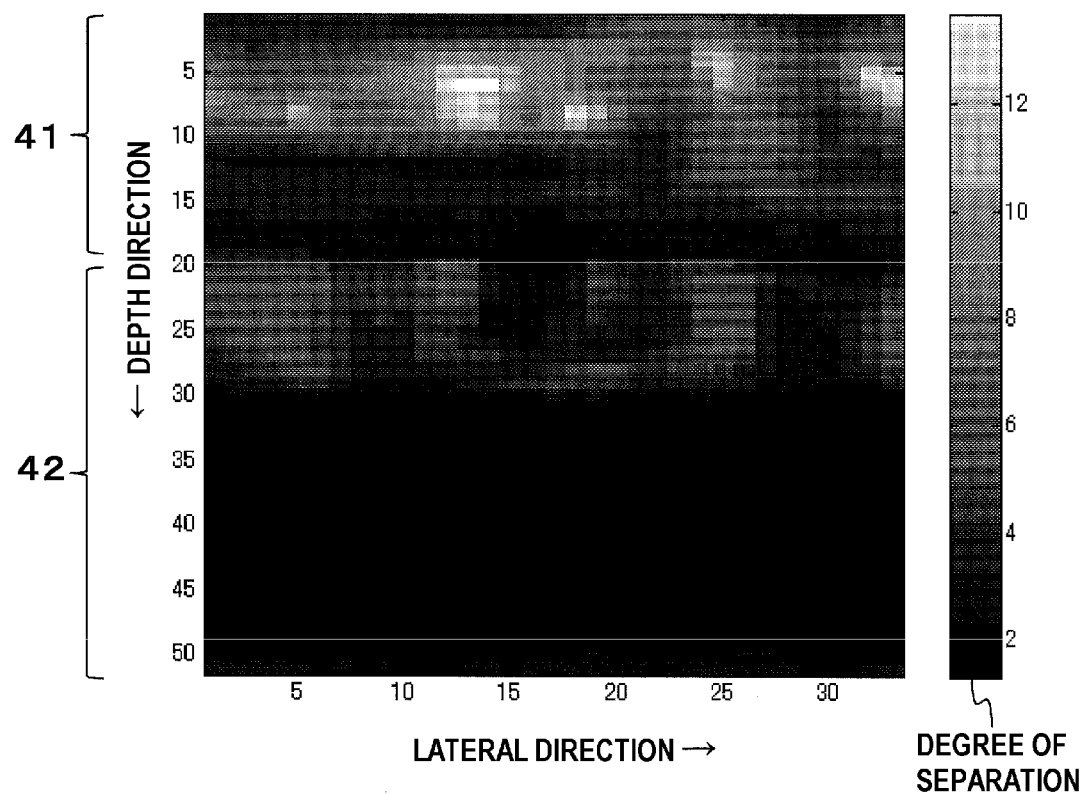
FIG. 9 illustrates an example of image being created based on the distribution of degrees of separation that is obtained in the process of FIG. 8.

FIG. 9 illustrates an image of the degree of separation obtained as to each of all the ROIs 31 in the step 83. It is found that in FIG. 9, 33×51 ROIs 31 are set in the frame m, and the degree of separation of each ROI 31 is represented by density. As shown in FIG. 9, the degree of separation is low in the low SNR area in the lower part of the frame m, and it is found that the degree of separation reflects the confidence in estimating the motion vectors.

In the process of FIG. 8 described above, the degree of separation is used. However, other index may be employed as the index for determining the degree of separation between the SAD minimum value and a SAD value with high frequency. By way of example, a coefficient of variation may be employed. The coefficient of variation is defined by the following formula. It is an amount of statistics obtained by standardizing the standard deviation by average, representing a dispersion size of the distribution (i.e., a degree of difficulty for separating the minimum value).

[Formula 3]

$$\text{Coefficient of Variation} \equiv \frac{\sigma_s}{\bar{s}} \quad (3)$$

Figure 10:
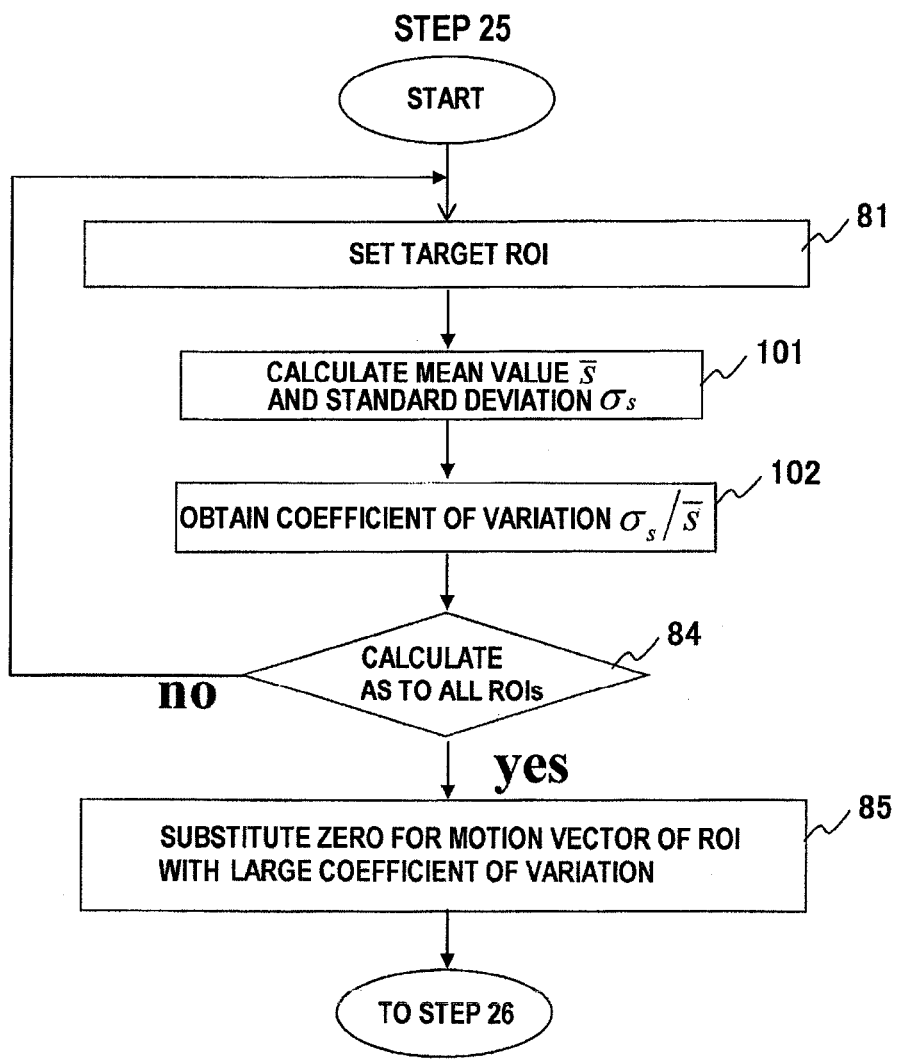
FIG. 10 is a flowchart showing the details of the process of the step 25 in FIG. 2, in the case where the process is performed through the use of a coefficient of variation.

FIG. 10 shows a flow of the process for removing the vectors in the area with much noise, in the case where the coefficient of variation is used as the index. Similar to the process flow of FIG. 8, a target ROI 31 is determined (step 81), and with regard to the ROI 31 being determined, a mean value and a standard deviation are calculated according to a statistical process, by using the SAD values of all the moving candidate regions 33 in the search area which is set and computed in the steps 52 and 53 of FIG. 3 (step 101). Then, the coefficient of variation defined by the aforementioned formula (3) is obtained (step 102). This procedure is repeated for all the ROIs (step 84). As for the ROI 31 having the coefficient of variation obtained in the step 102 being larger than a predetermined value, the motion vectors obtained in the step 54 of FIG. 3 are replaced by zero (step 85). Accordingly, it is possible to determine the ROI 31 with much noise, discriminating an area with low confidence from the motion vector image, and then, vectors (error vectors) are removed.

In the aforementioned step 85, it is possible to use as a predetermined value for determining whether or not the coefficient of variation is high, a predetermined threshold value or a median value in the distribution of the coefficients of variation obtained for all the ROIs 31 in the step 84. Alternatively, a histogram of the obtained coefficients of variation. may be generated. If there are two peaks of frequency, it is effective to employ as the predetermined value, a minimum value corresponding to a trough between the two peaks.

Figure 11:
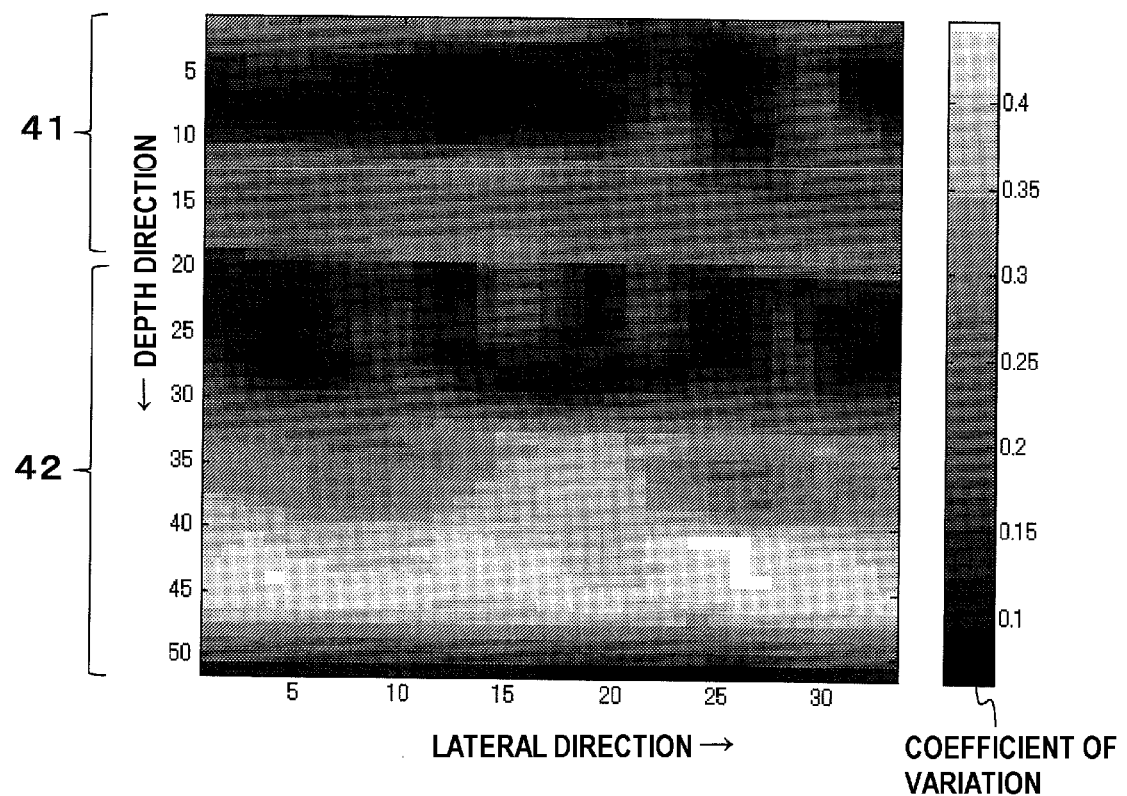
FIG. 11 illustrates an example of image being created based on the distribution of coefficients of variation that is obtained in the process of FIG. 10.

FIG. 11 illustrates an image of the coefficient of variation obtained as to each of all the ROIs 31 in the step 102. FIG. 11 represents the coefficient of variation of each ROI by density. As shown in FIG. 11, the coefficient of variation becomes larger in the low SNR corresponding to the lower portion of the frame m, and it is found that the coefficient of variation reflects the confidence in estimating the motion vectors.

Figure 12:
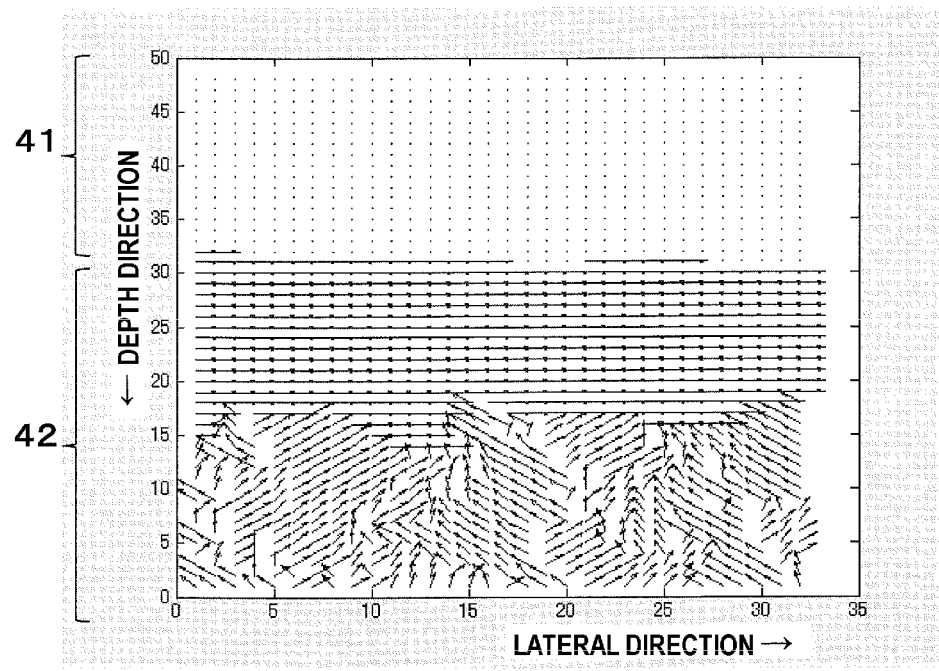
FIG. 12(a) illustrates an example of image of motion vector map created in the step 24 in FIG. 2.
FIG. 12(b) illustrates an example of image of vector map in which an error vector is removed in the step 25 of FIG. 2.
Figure 12:
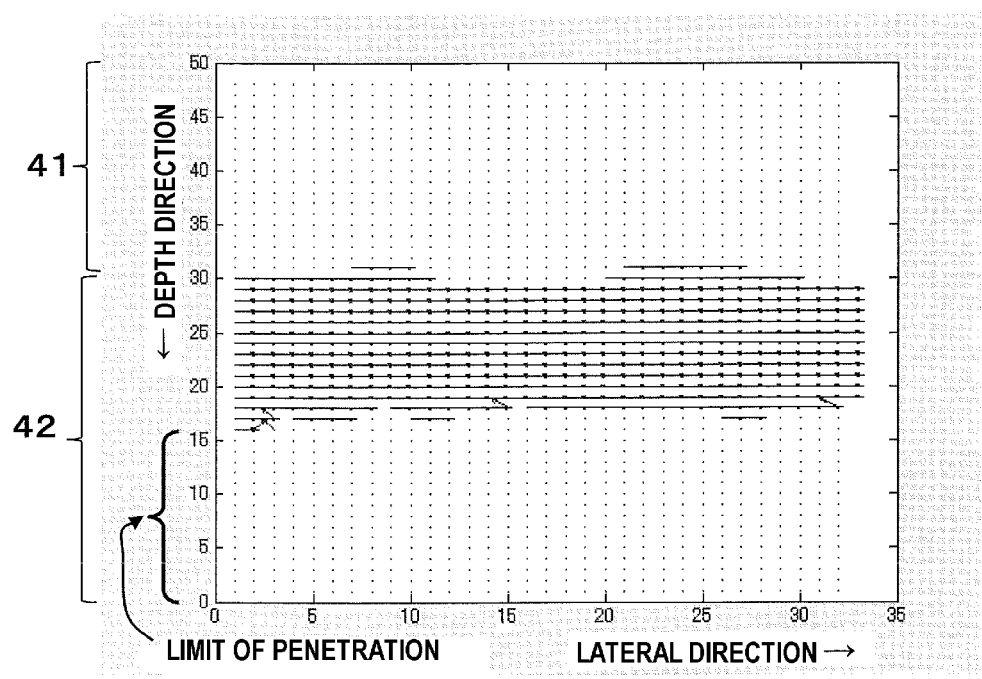

FIG. 12(*a*) and FIG. 12(*b*) illustrate examples of the motion vector map images, before and after removing the error vectors. FIG. 12(*a*) illustrates a motion vector field before removing the error vectors, in the same manner as that of FIG. 5(*b*). FIG. 12(*b*) illustrates that the distribution of coefficients of variation is obtained from the SAD distribution, according to the process in FIG. 10, a median value of the distribution of coefficients of variation is assumed as a threshold value, and it is determined that confidence of the ROI is low if the coefficient of variation of the ROI is larger than the threshold value, then setting the motion vectors to zero (static state). When FIG. 12(*a*) is contrasted with FIG. 12(*b*), in the lower area where the motion vectors fall into disorder, the error vectors are obviously removed, and the area is replaced with the static state. In other words, it is successfully determined that the lower area corresponds to a penetration area where ultrasonic echoes cannot be obtained accurately (i.e., an area of low confidence).

According to the processes as illustrated in FIG. 8 and FIG. 10 above, the error vectors in the motion vector map are removed. Then, according to the steps 26 and 27 in FIG. 2, the motion vector map is converted into a scalar map, and the scalar map image and the motion vector map image (or the B-mode image) are synthesized to be displayed.

In the processes in FIG. 8 and FIG. 10, the motion vectors in the area of low confidence are removed to bring the static state. However, the present invention is not limited to this processing method. By way of example, another processing method is possible to maintain the motion vector state to be the same state as it was obtained previously with regard to the same area, instead of setting the motion vectors to the static state.

(Second Embodiment)

In the first embodiment, after the SAD distribution is obtained, it is determined whether or not the ROI 31 corresponds to a low SNR area according to the SAD distribution. Then, if it corresponds to the low SNR area, processing is performed such as removing the motion vectors. On the other hand, in the present embodiment, noise is reduced at the time of computing the SAD distribution, and motion vectors with a high degree of confidence are obtained, by using the SAD distribution with high detection sensitivity after the noise has been reduced.

Figure 13:
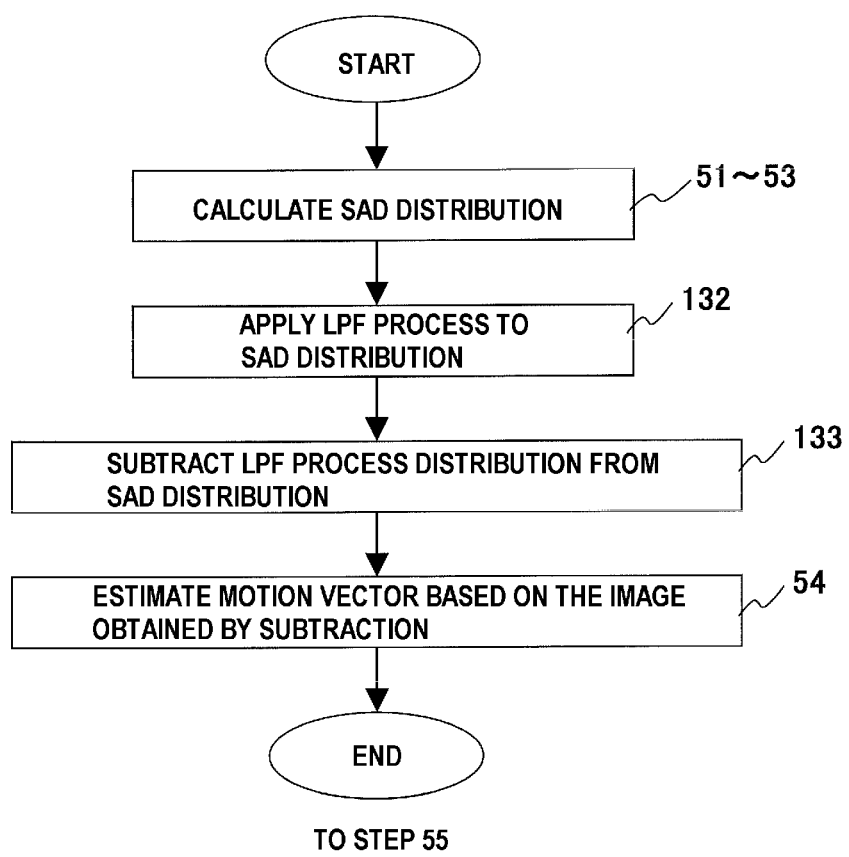
FIG. 13 is a flowchart of the process for reducing noise, when an operation is performed for the SAD distribution according to the second embodiment.
Figure 14:
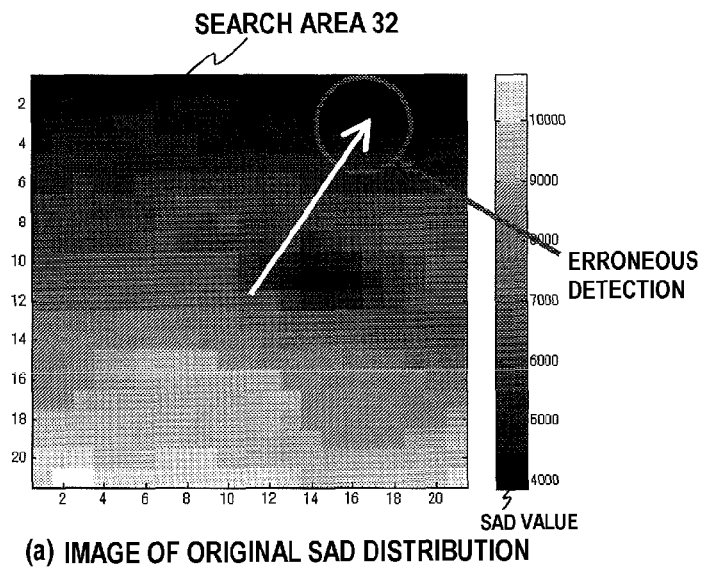
FIG. 14(a) illustrates an example of the SAD distribution image prior to the noise reduction according to the second embodiment.
FIG. 14(b) illustrates an example of the SAD distribution image obtained by applying smoothing (LPF) process to the SAD distribution image.
FIG. 14(c) illustrates an example of the SAD distribution image after the noise reduction.
Figure 14:
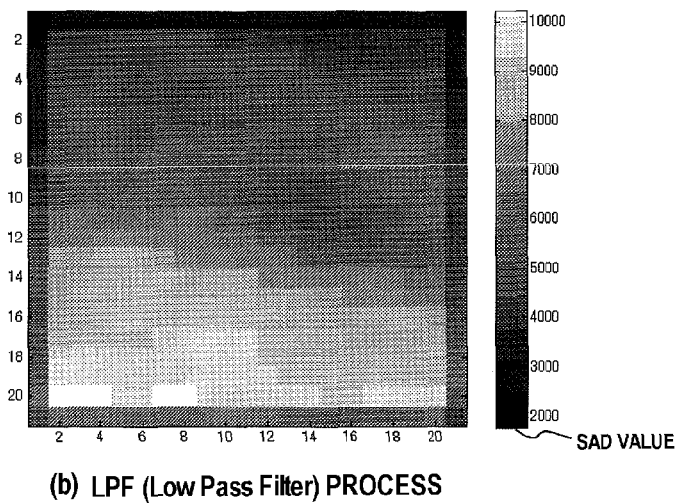
Figure 14:
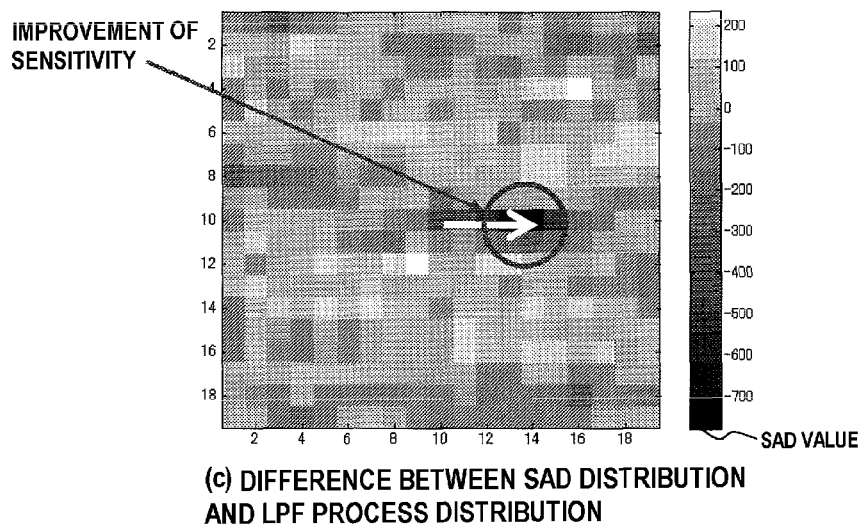

FIG. 13 is a processing flow for reducing the noise upon computing the SAD distribution, according to the second embodiment. In the process of FIG. 13, a noise reduction process (step 132 and step 133) is added to the SAD computing process which corresponds to the steps from 51 to 54 in FIG. 3 according to the first embodiment. FIGS. 14(*a*), (*b*), and (*c*) illustrate examples of the SAD distribution at each processing stages of FIG. 13.

As shown in FIG. 13, the processor 10 firstly carries out the processing which is the same as the processing from the steps 51 to 53 of FIG. 3, according to the first embodiment, so as to obtain the SAD distribution. FIG. 14(*a*) illustrates an example of the SAD distribution image being obtained. The ROI 31 corresponds to the position (4) of FIG. 5(*b*), and though the phantom 42 actually moves to a relatively lateral direction, the SAD value on the upper side becomes the minimum due to the effect of noise. Therefore, if the motion vector is determined without any change, vectors may be erroneously detected. In order to avoid such erroneous direction, the processor 10 subjects the SAD distribution image obtained in the steps 51 to 53 to a smoothing process (low pass filter (LPF) process) (step 132). Byway of example, the smoothing process filters the SAD distribution image through a predetermined size of filter, and the smoothing is carried out by cutting a high-frequency component of the SAD distribution in the filter. This process is repeated while moving the filter by a predetermined distance. As described above, according to the smoothing of the SAD distribution image, the change of SAD value due to the movement of the phantom 42 is filtered out because the change is steep, whereas the change of the SAD value due to the noise is very slow, and therefore it is extractable. FIG. 14(*b*) shows an SAD distribution image obtained by the smoothing process.

Next, a difference is obtained between the SAD distribution of the original step 53, and the SAD distribution after the smoothing process of the step 132 is performed (step 133). Accordingly, it is possible to obtain an intended SAD distribution caused by the phantom movement, where fluctuation of the SAD value due to the noise having been removed. FIG. 14(*c*) illustrates he distribution being obtained. The step 54 of FIG. 3 is executed through the use of the SAD distribution being obtained, and the moving candidate region 33 with the minimum SAD value is determined as a moving destination, thereby deciding the moving vectors. After the motion vectors are determined, a motion vector map image is generated by the process of the step 56 of FIG. 3 according to the first embodiment. It is possible to additionally perform the processing such as removing the vectors with low confidence from the motion vector map, in the step 25 of FIG. 2 according to the first embodiment.

As described above, according to the process of the second embodiment, the motion vectors can be determined by using the SAD distribution from which the SAD value fluctuation due to the noise has been removed, and therefore it is possible to enhance the confidence of the motion vectors.

It is to be noted that in the aforementioned smoothing process, the LPF is used. However, this is not the only example. If spatial frequency in the SAD distribution caused by the movement of the test object (phantom) is high (i.e., the shape is more complicated), it is effective to apply a band pass filter.

The size on a side of the filter which is used in the filtering process of the step 132 may be determined according to the following procedure. In other words, the process of the step 54 in FIG. 3 is performed in advance on the SAD distribution that has not been subjected to the smoothing process, so as to generate a motion vector field, and then a maximum vector length of the motion vector field is obtained. Then, the maximum vector length is set as the size on a side of the low pass filter or the band pass filter.

(Third Embodiment)

Next, as a third embodiment, a processing method will be explained for directly obtaining a tissue boundary by using the SAD distribution obtained in the step 53 of the first embodiment, and simultaneously determining a degree of invasion of a living-body tumor into a normal tissue. It is to be noted that in the third embodiment, the moving candidate region 33 in the search area 32 is simply referred to as a region 33. In addition, the ROI 31 is also referred to as a focused pixel.

Since the regions along the tissue boundary of the test object have a high degree of similarity of tissue, each region shows a close brightness level in the B-mode image. Therefore, the SAD shows a characteristic that it is a smaller value in the region 33 along the tissue boundary of the test object, than in the region 33 along the direction orthogonal to the boundary. On the other hand, when the invasion of the living-body tumor becomes deeper, the boundary becomes unclear, and therefore the SAD value in the region 33 along the boundary becomes larger. By the use of this fact, the degree of invasiveness is determined.

Figure 15:
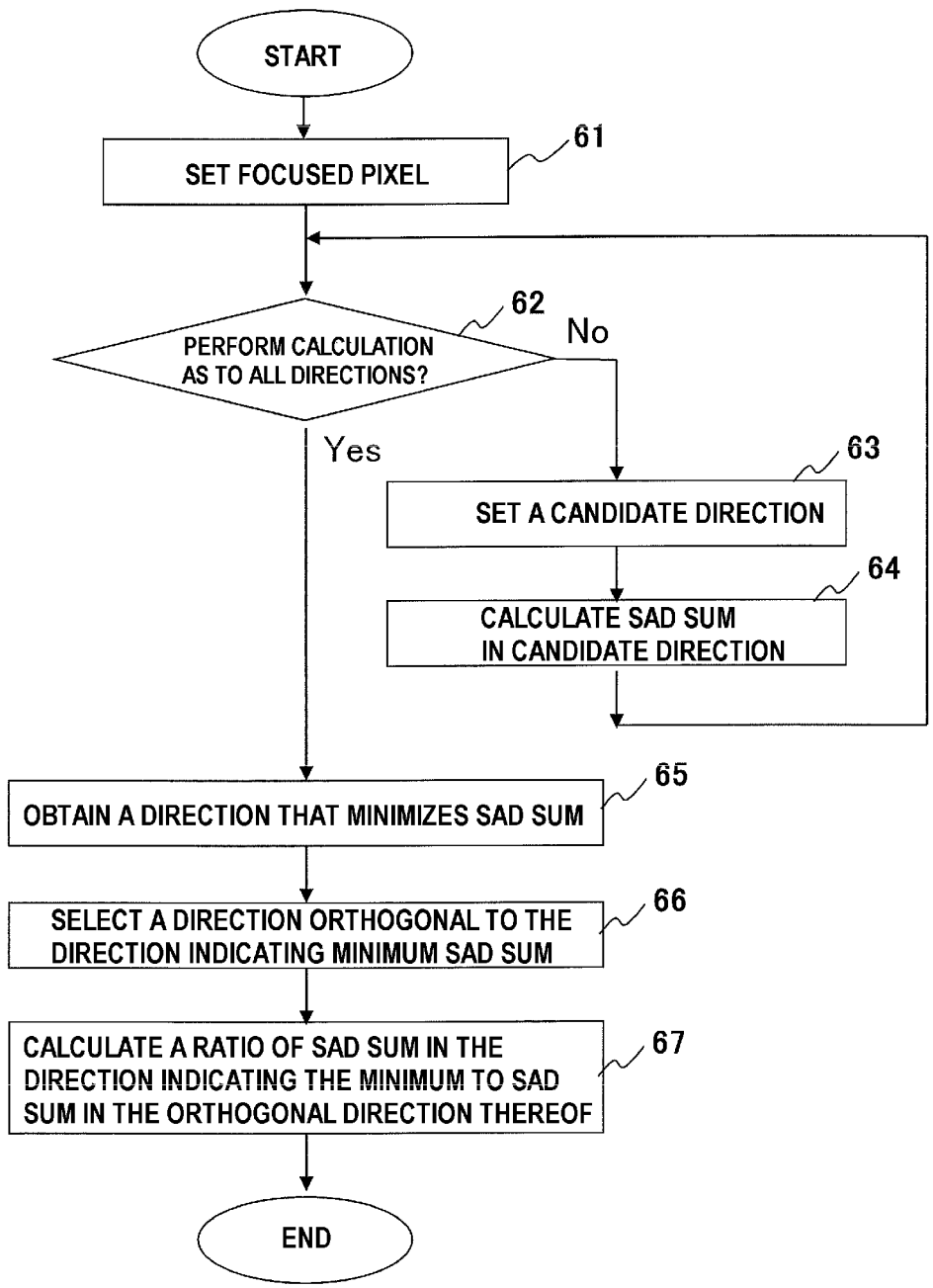
FIG. 15 is a flowchart showing a process for obtaining a degree of invasiveness according to a third embodiment.

FIG. 15 shows a processing flow of the processor 10 according to the third embodiment. FIG. 16(a) to FIG. 16(h) illustrate the targeted direction, and eight patterns of the regions 33 being selected on the SAD distribution image in association with targeted direction.

Firstly, the processor 10 sets a focused pixel (ROI) 31 at the boundary position of the tissue to be investigated, in a desired frame m of the B-mode image, sets a search area 32 at the frame m+Δ, and obtains the SAD distribution in the search area 32 (step 151). A method for selecting the frame and a computing method of the SAD distribution are carried out in the same manner as the steps 21 to 23 of FIG. 2 and the steps 51 to 53 of FIG. 3 according to the first embodiment.

Figure 16:
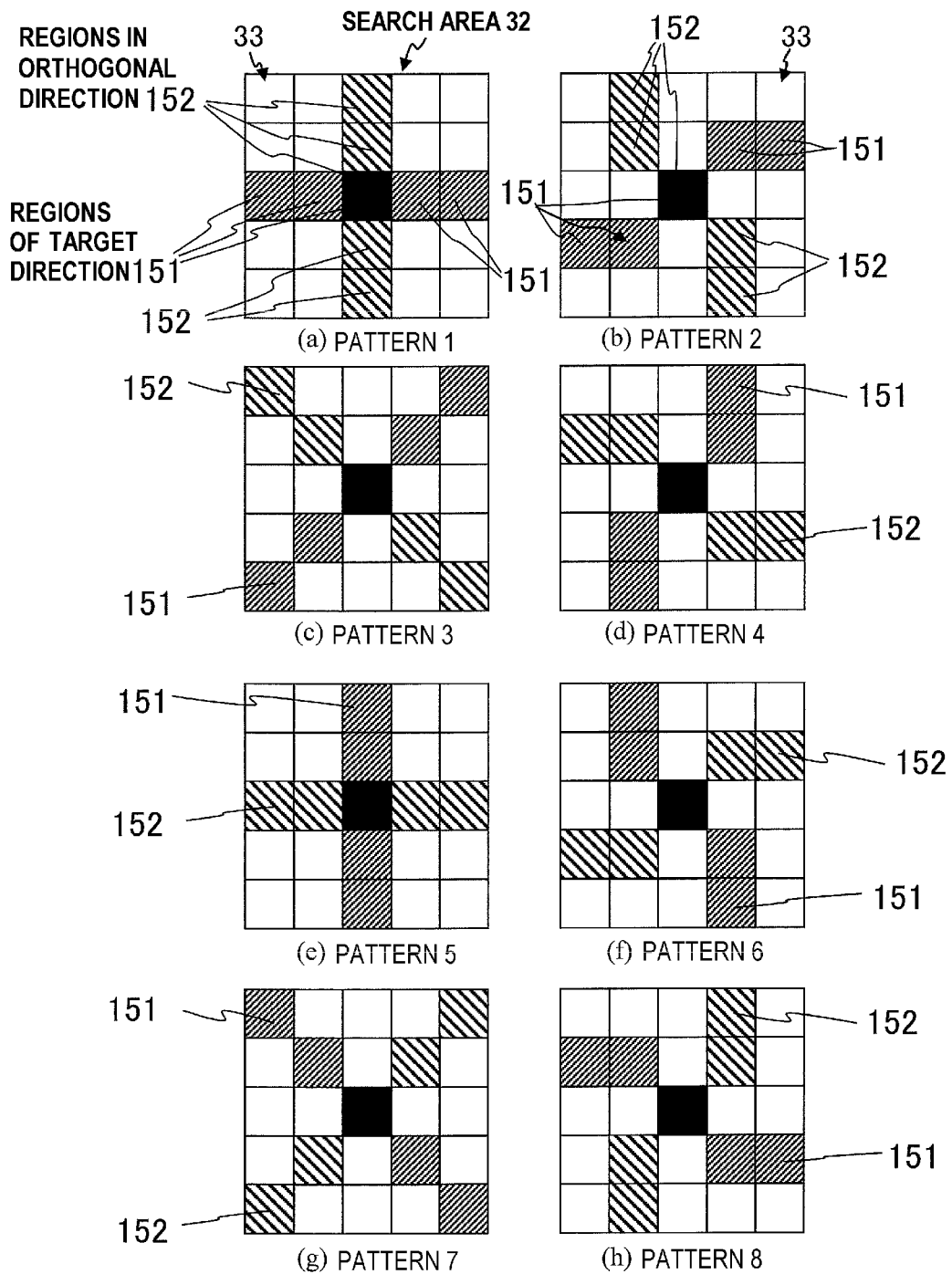
FIG. 16(a) to FIG. 16(h) illustrate region-selecting patterns of the SAD distribution used in the process of FIG. 15.

In the distribution of the SAD values, as shown in FIG. 16(a), the regions 33 passing through the center of the search area 32 and located along a predetermined target direction (horizontal direction) 151 are selected (step 63), and a sum of the SAD values within the selected regions 33 is obtained (step 64). Similarly, the regions 33 located along the direction (vertical direction) 152 orthogonal to the target direction 151 are selected, and a sum of the SAD values in the selected regions 33 is obtained.

The processing of the steps 63 and 64 is repeated until the processing on all the eight patterns of FIG. 16(a) to (h) is completed (step 62). In the pattern of FIG. 16(b), a sum of the SAD values is obtained in the regions 33 located along a predetermined target direction 151 (tilted at around 30° in anti-clockwise direction relative to the horizontal direction), and a sum of the SAD values is obtained in the regions 33 located along the direction 152 which is orthogonal to the direction above.

In the patterns of FIG. 16(c) to FIG. 16(h), a sum of the SAD values is obtained in the regions 33 located for each target direction 151, tilted at around 45°, around 60°, 90°, around 120°, around 135°, and around 150°, in anti-clockwise direction relative to the horizontal direction, and further a sum of the SAD values is obtained in the regions 33 located along the direction 152 which is orthogonal to each of the directions above.

The target direction 151 in which the sum of the SAD values becomes the minimum is selected out of the target directions 151 each of which the sum of the SAD values has been obtained (step 65). The direction of the selected target direction 151 indicates the direction of the tissue boundary. Accordingly, it is possible to directly detect the boundary without obtaining the motion vector.

Next, the direction 152 is selected, which is orthogonal to the target direction 151 being selected (step 66). A ratio of the sum of the SAD values in the selected target direction 151, to the sum of SAD values in the direction orthogonal thereto (the sum of SAD values in the target direction/the sum of SAD values in the orthogonal direction) is calculated (step 67).

If the degree of invasiveness is low and the boundary is definite, the sum of the SAD values in the boundary direction (the selected target direction 151) becomes small, and the sum of the SAD values in the orthogonal direction 152 becomes large. Therefore, a small value is obtained as the ratio. On the other hand, as the degree of invasiveness becomes higher, and the boundary becomes unclear, the sum of the SAD values in the boundary direction (selected target direction 151) is increased, and therefore, the ratio is getting higher. Therefore, it is possible to evaluate the degree of invasiveness, assuming the ratio as a parameter. Specifically, for instance, multiple reference values being predetermined are contrasted to the ratio, thereby determining the degree of invasiveness, and displaying the result of determination.

It is to be noted that if the ratio is smaller than a certain value being preset, the focused pixel (ROI) may be identified as a point constituting the boundary, thereby allowing the boundary to be displayed.

It is further to be noted that a directional adaptive filter may be employed to obtain the sum of the SAD values in each direction. The directional adaptive filter has a function to determine the direction in which a change in concentration in one-dimensional direction is the minimum, within the filter range (the search area 32) for the pixels to be processed.

In FIG. 16(a) to FIG. 16(h), in order to simplify the illustrations, region-selecting patterns are shown in the target direction 151 and in the orthogonal direction 152 within the search area 32 made up of 5×5 regions 33. However, in the actual processing, the region-selecting patterns are set, in association with the number of regions 33 within the search area 32.

(Fourth Embodiment)

As a fourth embodiment, another method will be explained for directly detecting the boundary, according to the SAD distribution in the search area 32, without obtaining the motion vectors. Here, a Laplacian filter is applied for performing an enhancement process in association with second derivation.

Figure 17:
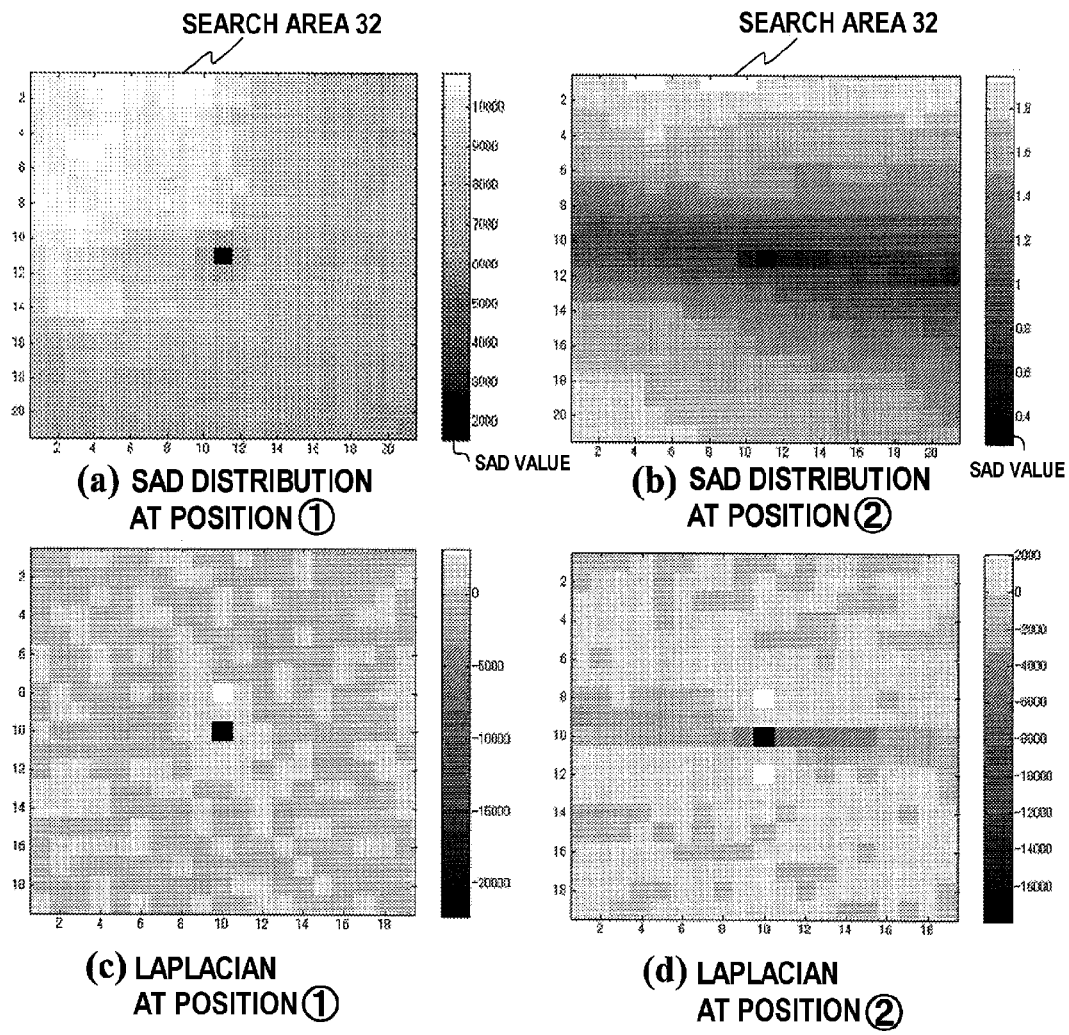
FIG. 17(a) illustrates an image of SAD distribution that is obtained by setting the ROI at the position (1) of FIG. 5(b)
FIG. 17(b) illustrates an image of the SAD distribution obtained by setting the ROI at the position (2) of FIG. 5(b)
FIG. 17(c) illustrates an image where the Laplacian filter is applied to the SAD distribution shown in FIG. 17(a)
FIG. 17(d) illustrates an image where the Laplacian filter is applied to the SAD distribution shown in FIG. 17(b).

In FIG. 17(a) and FIG. 17(b), the ROI 31 is set at the positions corresponding to the position (1) and the position (2) in FIG. 5(b), respectively, then showing the SAD distribution of the search area 32. The position (1) corresponds to the position inside the phantom 41 being relatively static with respect to the probe 1. The position (2) is located in the proximity of the boundary between the phantom 41 and the phantom 42 which moves in relatively lateral direction with respect to the phantom 41. The processing for obtaining the SAD distribution at the positions (1) and (2) is executed in the same manner as the steps 21 to 23 of the FIG. 2 and in the steps 51 to 53 of the FIG. 3. When the Laplacian filter for performing the second space derivation is applied to the obtained SAD distribution images (FIG. 17(a) and FIG. 17(b)), the images of FIG. 17(c) and FIG. 17(d) may be obtained, respectively, in which a part showing large variation of SAD values is enhanced by the edge enhancement effect.

If a boundary exists within the search area 32, as shown in FIG. 17(d), a distribution of edge enhancement is generated in which the regions with large variation of the SAD values along the boundary are enhanced and extracted in streaky form. Therefore, the regions along a continuous edge line (moving candidate regions 33) in the distribution of edge enhancement, are subjected to binary process, so as to extract the regions for displaying, thereby allowing the boundary to be detected from the Laplacian image of the SAD values. On the other hand, if no boundary exists within the search area 32, as shown in FIG. 17(c), the regions with large variation of SAD values only corresponds to the central area (the moving candidate region 33 associated with the position of ROI 31), being isolated from the surroundings, and it does not form a continuous edge line. Therefore, it is found that there is no boundary at this position.

According to the processing above, the SAD distribution is subjected to the Laplacian process, thereby enabling direct extraction of the boundary. Therefore, it is possible to eliminate the steps 54 and 55 of FIG. 3 for deciding the motion vectors for creating an image according to the first embodiment, and the steps 25 and 26 of FIG. 2 for reducing noise in the motion vectors and executing the conversion into a scalar map so as to estimate the boundary. Consequently, this enables a drastic cut of throughput.

Industrial Applicability

The present invention is applicable to a medical-use ultrasonic diagnostic and treatment device, and to a general device for measuring a strain or displacement, by using any kind of electromagnetic waves including ultrasonic waves.

Explanation of References

1: ULTRASONIC PROBE (PROBE), 2: USER INTERFACE, 3: TRANSMISSION WAVE BEAM FORMER, 4: CONTROL SYSTEM, 5: TRANSMIT-RECEIVE CHANGEOVER SWITCH, 6: RECEIVED WAVE BEAM FORMER, 7: ENVELOPE DETECTOR, 8: SCAN CONVERTER, 10: PROCESSOR, 10a: CPU, 10b: MEMORY, 11: PARAMETER SETTER, 12: SYNTHESIZER, 13: MONITOR

What is claimed is:

1. An ultrasonic imaging apparatus comprising:
   a transmitter configured to transmit ultrasonic waves directed to an object;
   a receiver configured to receive ultrasonic waves coming from the object, and to output signals representing the received ultrasonic waves to the processor; and
   a processor configured to process signals received from the receiver, and to generate an image a including plurality of frames;
   wherein the processor is configured to:
      assume one frame as a reference frame, in the image including a plurality of frames being generated,
      set a region of interest at either of a predetermined position and a position accepted from an operator,
      assume another one frame as a comparative frame,
      set a search area wider than the region of interest, at either of a predetermined position and a position accepted from an operator,
      set multiple candidate regions in the search area, which are destination candidates of the region of interest,
      calculate a degree of similarity between an image characteristic value in the region of interest and an image characteristic value in the candidate region, with respect to each of the candidate regions, so as to obtain a similarity distribution of the degrees of similarity across the search area; and
      obtain statistics that compare a minimum value of the degree of similarity with an overall value of the degree of similarity in the similarity distribution, by using the minimum value of the degree of similarity, a mean value of the degree of similarity, and a standard deviation of the degree of similarity, and compares the obtained statistics with a threshold value, thereby determining the confidence of the region of interest.

2. The ultrasonic imaging apparatus according to claim 1, wherein the processor is configured to generate a vector which connects a position associated with the region of interest in the comparative frame, to a position of the candidate region with the minimum degree of similarity, and to substitute zero or a predetermined vector for the vector with regard to the region of interest determined as having low confidence.

3. The ultrasonic imaging apparatus according to claim 1, wherein the processor is configured to calculate a mean value, the minimum value, and a standard deviation of the degree of similarity, with regard to the similarity distribution, and to obtain as the statistics, a degree of separation obtained by dividing a difference between the mean value and the minimum value, by the standard deviation.

4. The ultrasonic imaging apparatus according to claim 1, wherein the processor is configured to calculate a mean value and a standard deviation of the degree of similarity, with regard to the similarity distribution, and to obtain as the statistics, a coefficient of variation obtained by dividing the standard deviation by the mean value.

5. The ultrasonic imaging apparatus according to claim 1 wherein the processor is configured to set multiple regions of interest, to obtain statistics with respect to each of the regions of interest, to obtain a histogram distribution representing a frequency of values of the statistics obtained, and to use, as the threshold value, a median value or a mean value of the histogram distribution, or if the histogram distribution shows multiple peaks, a minimum value of the statistics associated with a trough between the peaks.

6. The ultrasonic imaging apparatus according to claim 1, wherein the processor is configured to perform a smoothing process on the similarity distribution, and to subtract the resulting similarity distribution after the smoothing process from the similarity distribution prior to the smoothing process, thereby obtaining a differential similarity distribution.

7. The ultrasonic imaging apparatus according to claim 6, wherein the smoothing process is configured to set a filter of a predetermined size on the similarity distribution, and to repeat a process for smoothing the distribution within the filter, while moving the filter by a predetermined distance; and
   wherein the processor is configured to generate a vector with respect to each of multiple regions of interest, a vector connecting a position associated with the region of interest in the comparative frame, to the position of the candidate region with the minimum degree of similarity in the similarity distribution prior to the smoothing process, and to assume a maximum length of the vector, out of the vectors generated, as the size of the filter.

8. The ultrasonic imaging apparatus according to claim 1, wherein the processor is configured to subject the similarity distribution to a filtering process using a Laplacian filter, thereby creating a distribution of edge enhancement, and to extract a continuous edge from the distribution of edge enhancement, thereby obtaining a boundary of the object.

9. The ultrasonic imaging apparatus according to claim 1, wherein, the processor comprises,
   a first processing means for obtaining the similarity distribution as to the region of interest set near a boundary of a tumor in a living body, generating a similarity distribution image assuming the degree of similarity as an image characteristic value, and setting an one-dimensional area with a predetermined length in each of multiple different directions with a central focus on a position associated with the region of interest on the similarity distribution image;

a second processing means for calculating a total sum of the degrees of similarity within the one-dimensional area, with respect to each of the directions set;

a third processing means for calculating a ratio of a total sum of the degrees of similarity in the direction in which the total sum of the degrees of similarity becomes the minimum, to a total sum of the degrees of similarity of the one-dimensional area in the direction orthogonal to the direction in which the total sum of the degrees of similarity becomes the minimum; and a fourth processing means for determining a degree of invasiveness of the tumor based on the ratio.

10. The ultrasonic imaging apparatus according to claim 9, wherein when the ratio calculated in the third processing means is smaller than a predetermined certain value, the processor is configured to determine that the region of interest corresponds to a point constituting the boundary.

* * * * *